United States Patent
Schoepgens et al.

(10) Patent No.: US 10,667,997 B2
(45) Date of Patent: Jun. 2, 2020

(54) THICKENED OXIDATION COMPOSITION

(71) Applicant: Henkel AG & Co. KGaA, Duesseldorf (DE)

(72) Inventors: Juergen Schoepgens, Schwalmtal (DE); Torsten Lechner, Langenfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/224,240

(22) Filed: Dec. 18, 2018

(65) Prior Publication Data
US 2019/0183750 A1    Jun. 20, 2019

(30) Foreign Application Priority Data
Dec. 20, 2017  (DE) .................. 10 2017 223 320

(51) Int. Cl.
| | | |
|---|---|---|
| *A61K 8/22* | (2006.01) | |
| *A61Q 5/04* | (2006.01) | |
| *A61K 8/81* | (2006.01) | |
| *A61K 8/92* | (2006.01) | |
| *A61K 8/06* | (2006.01) | |
| *A61Q 5/08* | (2006.01) | |
| *A61Q 5/06* | (2006.01) | |
| *A61K 8/86* | (2006.01) | |

(52) U.S. Cl.
CPC .............. *A61K 8/22* (2013.01); *A61K 8/064* (2013.01); *A61K 8/8147* (2013.01); *A61K 8/86* (2013.01); *A61K 8/92* (2013.01); *A61Q 5/04* (2013.01); *A61Q 5/065* (2013.01); *A61Q 5/08* (2013.01); *A61K 2800/4322* (2013.01); *A61K 2800/882* (2013.01)

(58) Field of Classification Search
None
See application file for complete search history.

(56) References Cited

U.S. PATENT DOCUMENTS

2018/0168941 A1*  6/2018  Schoepgens ........... A61K 8/042

FOREIGN PATENT DOCUMENTS

| DE | 10 2011 087 980 A1 | 9/2012 |
|---|---|---|
| DE | 10 2016 225 382 A1 | 6/2018 |
| GB | 2558078 A | 7/2018 |
| GB | 2561642 A | 10/2018 |
| GB | 2561938 A | 10/2018 |
| GB | 2562135 A | 11/2018 |
| GB | 2562136 A | 11/2018 |
| GB | 2562816 A | 11/2018 |

* cited by examiner

*Primary Examiner* — Celeste A Roney
(74) *Attorney, Agent, or Firm* — Lorenz & Kopf, LLP

(57) ABSTRACT

The present disclosure relates to an oxidising agent composition (M2), a packaging unit (kit of parts) comprising an agent for oxidative hair dyeing (M1) (dye component) and the oxidising agent composition (M2), a method for oxidative hair dyeing with use of the oxidising agent composition (M2), and the use of the oxidising agent composition for oxidative hair dyeing, for oxidative bleaching or lightening, and as fixing agent in a method for permanent shaping.

16 Claims, No Drawings

THICKENED OXIDATION COMPOSITION

CROSS-REFERENCE TO RELATED APPLICATION

This application claims priority to German Patent Application No. 10 2017 223 320.6, filed Dec. 20, 2017, which is incorporated herein by reference in its entirety.

TECHNICAL FIELD

The present application relates to an oxidising agent composition (M2), a packaging unit (kit of parts) comprising an agent for oxidative hair dyeing (M1) (dye component) and the oxidising agent composition (M2), a method for oxidative hair dyeing with use of the oxidising agent composition (M2), and the use of the oxidising agent composition for oxidative hair dyeing, for oxidative bleaching or lightening, and as fixing agent in a method for permanent shaping.

BACKGROUND

In order to provide colouring agents for keratin fibres, in particular for human hair, a person skilled in the art is aware of various dye systems depending on the demands placed on the colouring. What are known as oxidation dyes are used for permanent, intense colourations having appropriate fastness properties. Such colouring agents usually contain oxidation dye precursors, so-called developer components and coupler components, which create the actual dyes among each other under the influence of oxidising agents or atmospheric oxygen. The oxidation dyes are exemplified by excellent long-lasting dyeing results. Besides colouring, the lightening of the natural hair colour or bleaching is a very specific desire of many consumers. To this end, the natural or artificial colourants colouring the fibres are usually oxidatively decolorised with the use of appropriate oxidising agents, such as hydrogen peroxide. For temporary dyeing, dyes or toners which contain what are known are substantive dyes (direct dyes). These can be used likewise together with oxidising agents in lightening colouring agents.

In order to develop optimal dyeing power, oxidative dyes generally require an alkaline pH value for the colouring, in particular between from about pH 8.5 and about pH 11.5. For reasons of stability, oxidative dyes are usually produced only just before application, by mixing a dye component (agent for oxidative hair dyeing) and an oxidising agent composition. The dye component usually has an alkaline pH value for stabilisation of oxidation dye precursor products, and the oxidising agent composition usually has an acidic pH value for stabilisation of the oxidising agent, whereas the ready-to-use mixture should have an alkaline pH value so as to enable good penetration of the dye precursor products and the oxidising agent into the keratin fibres.

In addition, the application period for satisfactory dyeing results is usually between from about 10 and about 60 minutes. The ready-to-use colouring agent should therefore be formulated and packaged such that the colouring agent on the one hand can be easily distributed over the keratin fibres to be dyes, but on the other hand remains in the fibres to be coloured during the application time. To this end it is advantageous if the colouring agent has a certain viscosity which makes it possible to apply the agent, but which also leaves the agent behind at the site of use. This viscosity can be adjusted by polymer thickeners in the ready-to-use colouring agent, wherein this thickener can be contained both in the dye component or the oxidising agent composition.

The aforementioned oxidising agent compositions and dye components are usually incorporated into a cosmetically suitable carrier, such as a cream. The carrier ensures the above-mentioned homogeneous distribution and a sufficient residence time of the hair colouring agent on the hair.

A disadvantage is the complex production of a cream of this kind. A lot of energy is required for the melting of the fat components and the emulsification. The subsequent cooling consumes large amounts of cooling water.

Due to high fat components in conventional creams, continuous production can be implemented only with difficulty. Here, the constituents in the melt must be provided in such a ratio to one another to ensure pumpability.

BRIEF SUMMARY

Oxidising agent compositions for treating keratin fibers, and methods and uses thereof are provided herein. In an exemplarily embodiment, an oxidising agent composition includes hydrogen peroxide and at least one sodium polyacrylate pre-gelled in a water-in-oil emulsion, wherein the water-in-oil emulsion, in relation to the weight of the water-in-oil emulsion, comprises from about 40 to about 60% by weight sodium polyacrylate, from about 25 to about 45% by weight oil(s), from about 0.5 to about 4.9% by weight surfactant(s), and from about 0.5 to about 4.9% by weight water.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was to provide an oxidising agent composition which can be produced under the most economical and sustainable conditions possible. A further object of the present disclosure was to provide an oxidising agent composition which can be packaged under the most economical and sustainable conditions possible. A further object of the present disclosure was to provide an oxidising agent composition that can be produced continuously.

A further object of the present disclosure was to provide an oxidising agent composition which is exemplified by very good miscibility of the oxidising agent composition and a dye component.

Furthermore a colouring agent which contains the oxidising agent composition should be exemplified by good longevity on the keratin fibres, simple application and generally quick reaction times, and should lead to good optical results, for example in respect of the dyeing performance and fastness properties.

These objects are solved by an oxidising agent composition (M2) containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water.

The oxidising agent composition (M2) preferably constitutes the oxidising agent of an oxidative hair colouring agent. This is usually mixed directly before use with a dye component and then applied to the hair to be coloured. Apart from the mixing with the dye component, the oxidising agent composition as contemplated herein does not contain any dyes.

In a further embodiment preferred as contemplated herein the oxidising agent composition (M2) as contemplated herein constitutes a fixing agent for permanently shaped hair. As fixing agent, the oxidising agent composition (M2) as contemplated herein is applied as such to the hair to be fixed following the use of a keratin-reducing agent, for example a thioglycolate-containing composition. A method of this kind is usually used in the case of permanent waving or hair straightening.

In a further embodiment preferred as contemplated herein the oxidising agent composition (M2) as contemplated herein constitutes a lightening agent for hair. Lightening agents of this kind are usually used to extend the lightening effect of a bleaching agent. As lightening agent, the oxidising agent composition (M2) as contemplated herein can be used in the form of a leave-in agent by being applied to the hair to be lightened, for example sprayed on, without then being rinsed out.

Keratin fibres, keratin-containing fibres or keratinous fibres are understood to mean fur, wool, feathers and in particular human hair. Although the agents as contemplated herein are suitable primarily for lightening and dyeing keratin fibres, there is in principle also nothing against use in other areas.

A characterising feature of the oxidising agent composition (M2) as contemplated herein is the presence of sodium polyacrylate pre-gelled in a water-in-oil emulsion in addition to hydrogen peroxide. The above-mentioned problems are solved by the oxidising agent composition as contemplated herein, in particular in an oxidising agent composition in the form of a cream, an emulsion or a gel.

(a) Sodium Polyacrylate Pre-Gelled in a Water-in-Oil Emulsion

An essential feature of the oxidising agent composition as contemplated herein is the presence of sodium polyacrylate which is present in the form of sodium polyacrylate pre-gelled in a water-in-oil emulsion, wherein the sodium polyacrylate-containing water-in-oil emulsion, in each case in relation to its total weight (of about 100% by weight), contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water.

The oil contained in the sodium polyacrylate-containing water-in-oil emulsion is particularly preferably selected from natural and synthetic hydrocarbons, particularly preferably from mineral oil, paraffin oils, $C_{18}$-$C_{30}$ isoparaffins, in particular isoeicosan, polyisobutenene and polydecenene, $C_8$-$C_{16}$ isoparaffins, and 1,3-di-(2-ethylhexyl)-cyclohexane; the benzoic acid esters of linear or branched $C_{8-22}$ alkanols; triglycerides of linear or branched saturated or unsaturated, optionally hydroxylated $C_{8-30}$ fatty acids, in particular natural oils; the dicarboxylic acid esters of linear or branched $C_2$-$C_{10}$ alkanols; the esters of linear or branched saturated or unsaturated fatty alcohols with from 2 to 30 carbon atoms with linear or branched saturated or unsaturated fatty acids with from 2 to 30 carbon atoms, which may be hydroxylated; the addition products of from about 1 to about 5 propylene oxide units with mono- or polyvalent $C_{8-22}$ alkanols the $C_8$-$C_{22}$ fatty alcohol esters of monovalent or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the ester of dimers of unsaturated $C_{12}$-$C_{22}$ fatty acids (dimer fatty acids) with monovalent linear, branched or cyclic $C_2$-$C_{18}$ alkanols or with polyvalent linear or branched $C_2$-$C_6$ alkanols; silicone oils and mixtures of the aforementioned substances. An oil that is particularly preferred as contemplated herein is mineral oil.

The surfactant contained in the sodium polyacrylate-containing water-in-oil emulsion is particularly preferably selected from non-ionic surfactants ('niosurfactants'). Non-ionic surfactants used with particular preference are selected from castor oil ethoxylated with from about 7 to about 80 mol ethylene oxide per mol, ethoxylated $C_8$-$C_{24}$ alkanols with from about 5 to about 30 mol ethylene oxide per mol, ethoxylated $C_8$-$C_{24}$ carboxylic acids with from about 5 to about 30 mol ethylene oxide per mol, sorbitol monoesters of linear saturated and unsaturated $C_{12}$-$C_{30}$ carboxylic acids ethoxylated with from about 4 to about 50 mol ethylene oxide per mol, which may be hydroxylated, in particular those of myristic acid, palmitic acid, stearic acid or mixtures of these fatty acids, alkylmono- and -oligoglycosides with from 8 to 22 carbon atoms in the alkyl group and the ethoxylated analogues thereof, and mixtures of the aforementioned substances.

The ethoxylated $C_8$-$C_{24}$ alkanols have the formula $R^1O(CH_2CH_2O)_nH$, wherein $R^1$ stands for a linear or branched alkyl and/or alkenyl group with from 8 to 24 carbon atoms and n, the mean number of ethylene oxide units per molecule, stands for numbers of from about 5 to about 30, preferably from about 6 to about 20, particularly preferably from about 6 to about 12 mol ethylene oxide with 1 mol alkanol, which is preferably selected from capryl alcohol, 2-ethylhexyl alcohol, capric alcohol, lauryl alcohol, isotridecyl alcohol, tridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and also technical mixtures thereof. Adducts of from about 10 to about 100 mol ethylene oxide with technical fatty alcohols having from 12 to 18 carbon atoms, such as coconut, palm, palm kernel or tallow fatty alcohol, are also suitable. Particularly preferred are Trideceth-6, Isotrideceth-6, Undeceth-6, Myreth-6, Laureth-10, Laureth-12, Laureth-15, Laureth-20, Laureth-30, Myreth-10, Myreth-12, Myreth-15, Myreth-20, Myreth-30, Ceteth-10, Ceteth-12, Ceteth-15, Ceteth-20, Ceteth-30, Steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30 and also Coceth-10, Coceth-12, Coceth-15, Coceth-20 and Coceth-30; exceptionally preferred are Trideceth-6 and Isotrideceth-6 and mixtures hereof.

The ethoxylated $C_8$-$C_{24}$ carboxylic acids have the formula $R^1O(CH_2CH_2O)_nH$, wherein $R^1O$ stands for a linear or branched saturated or unsaturated acyl group with from 8 to 30 carbon atoms and n, the mean number of ethylene oxide units per molecule, stands for numbers of from about 5 to about 30, preferably from about 6 to about 20, particularly preferably from about 6 to about 12 mol ethylene oxide with about 1 mol $C_8$-$C_{30}$ carboxylic acid, which is preferably selected from caprylic acid, 2-ethylhexanoic acid, capric acid, lauric acid, isotridecanoic acid, myristic acid, cetylic acid, palmitoleic acid, stearic acid, isostearic acid, oleic acid, elaidic acid, petroselinic acid, arachyic acid, gadoleic acid, behenic acid, erucic acid and brassidic acid and also technical mixtures thereof. Adducts of from about 5 to about 30, preferably from about 6 to about 20, particularly preferably from about 6 to about 12 mol ethylene oxide with technical fatty alcohols having from about 12 to about 18 carbon atoms, such as coconut, palm, palm kernel or tallow fatty alcohol, are also suitable.

Oxidising agent compositions that are exceptionally preferred as contemplated herein are exemplified in that they contain at least one sodium polyacrylate with a weight-average molar mass $M_w$ in the range of from about 1,000,000 to about 20,000,000 Dalton, preferably from about 6,000,000 to about 15,000,000 Dalton, wherein the sodium polyacrylate is contained pre-gelled in a water-in-oil emulsion, wherein said water-in-oil emulsion, in each case in relation to its total weight, contains from about 40 to about 60% by weight sodium polyacrylate, a total of from about 25 to about 45% by weight oil(s), preferably mineral oil, a total of from about 0.5 to about 4.9% by weight surfactant(s), preferably from about 0.5 to about 4.9% by weight niosurfactant(s), and from about 0.5 to about 4.9% by weight water.

The sodium polyacrylate is contained in the oxidising agent composition as contemplated herein generally in a total amount of from about 0.1 to about 2% by weight, preferably from about 0.2 to about 1.5% by weight, in each case in relation to the weight of the oxidising agent composition.

The water-in-oil emulsion containing the pre-gelled sodium polyacrylate is contained in the oxidising agent composition as contemplated herein generally in a total amount of from about 0.2 to about 3% by weight, preferably from about 0.5 to about 2% by weight, in each case in relation to the weight of the oxidising agent composition.

(b) Hydrogen Peroxide

Hydrogen peroxide is used as oxidising agent in the oxidising agent composition as contemplated herein.

Hydrogen peroxide is used here either as preferably aqueous solution or in the form of a solid addition compound of hydrogen peroxide with inorganic or organic compounds, such as sodium perborate, sodium percarbonate, magnesium percarbonate, sodium percarbamide, polyvinylpyrrolidone n $H_2O_2$ (n is a positive integer greater than about 0), urea peroxide and melamine peroxide. Aqueous hydrogen peroxide solutions are used with preference as contemplated herein. The concentration of a hydrogen peroxide solution is determined on the one hand by the legal requirements and on the other hand by the desired effect. From about 3% by weight to about 12% by weight solutions of hydrogen peroxide in water are preferably used.

Generally, the oxidising agent composition as contemplated herein contains hydrogen peroxide in an amount of from about 0.5 to about 23% by weight, preferably from about 2.5 to about 21% by weight, particularly preferably from about 4 to about 20% by weight, very particularly preferably from about 5 to about 18% by weight, exceptionally preferably from about 6 to about 12% by weight, in each case in relation to the weight of the oxidising agent composition, calculated as about 100% $H_2O_2$.

The viscosity of the oxidising agent composition as contemplated herein is generally from about 500 to about 7000 mPas, preferably from about 1500 to about 4000 mPas, in each case measured at about 20° C., Haake MV 2.

In order to stabilise the hydrogen peroxide, the oxidising agent composition as contemplated herein has a pH value in the range of from about 1.0 to about 6.5, preferably from about 1.4 to about 5.5, particularly preferably from about 2.8 to about 4, exceptionally preferably from about 3 to about 3.8, in each case measured at about 20° C. Conventional acidification and alkalising agents for adjusting the pH value are known to a person skilled in the art. Acidification means that are preferred as contemplated herein are edible acids, such as lactic acid, citric acid, malic acid or tartaric acid, and diluted mineral acids, in particular phosphoric acid.

It can be preferred if the oxidising agent composition as contemplated herein also—besides the above-mentioned components—contains surface-active, in particular anionic surface-active substances which are different from the above-mentioned surfactants. One embodiment of the present disclosure is therefore exemplified in that the oxidising agent composition as contemplated herein additionally contains at least one anionic surfactant in a proportion by weight of from about 0.05 to about 1.5% by weight, in relation to the total weight of the oxidising agent composition.

Emulsifiers and surfactants are suitable surface-active substances as contemplated herein. Surface-active substances are exemplified by hydrophobic and hydrophilic structural features and thus make it possible to thoroughly mix the phases, forming micelles and stable emulsions. Anionic surfactants as contemplated herein are all anionic surface-active substances suitable for use on the human body. These are exemplified by a water-soluble-making anionic group, such as a carboxylate, sulfate, sulfonate or phosphate group and a lipophilic alkyl group having approximately 8 to 30 C atoms. In addition, glycol or polyglycolether groups, ester, ether and amide groups and also hydroxyl groups can be contained in the molecule. Examples of such anionic surfactants are, in each case in the form of the sodium, potassium and ammonium and also the mono- di- and trialkanol ammonium salts with from 2 to 4 C atoms in the alkanol group, linear and branched fatty acids with from 8 to 30 C atoms (soaps): ethercarboxylic acids, in particular of formula $RO(CH_2CH_2O)xCH_2COOH$, in which R is a linear alkyl group with from 8 to 30 C atoms and x=0 or is from 1 to 16; acyl sarcosides; acyl taurides; acyl isethionates; sulfosuccinic acid monoesters and dialkylesters and sulfosuccinic acid mono-alkylpolyoxyethyl esters; linear alkane sulfonates; linear alpha-olefin sulfonates; sulfonates of unsaturated fatty acids; alpha-sulfo fatty acid methyl esters of fatty acids; alkylsulfates and alkylether sulfates, in particular of formula $RO(CH_2CH_2O)xSO_3H$, in which R stands for a linear alkyl group with from 8 to 30 C atoms and x stands for about 0 or a number from about 1 to about 12; mixtures of surface-active hydroxy sulfonates; sulfated hydroxyalkyl polyethylene and/or hydroxyalkylene propylene glycol ether; esters of tartaric acid and citric acid with alcohols; alkyl and/or alkenyl ether phosphates of formula $RO(C_2H_4O)xP(\text{=}O)(OH)(OR')$, in which R stands for an aliphatic, optionally unsaturated hydrocarbon group with from 8 to 30 carbon atoms, R' stands for hydrogen, a group $(CH_2CH_2O)_yR$, and x and y independently of one another stand for a number from 1 to 10; sulfated fatty acid alkylene glycol esters of formula $RC(O)O(alkO)nSO_3H$, in which R stands for a linear or branched, aliphatic, saturated and/or unsaturated alkyl group with from 6 to 22 C atoms, alk stands for $CH_2CH_2$, $CHCH_3CH_2$ and/or $CH_2CHCH_3$ and n stands for a number from about 0.5 to about 5; and also monoglyceride sulfates and monoglyceride ether sulfates.

As contemplated herein the oxidising agent composition can be applied to the keratin fibres, in particular human hair, together with a catalyst, which additionally activates the oxidation of the dye precursor products. Such catalysts are, for example, certain enzymes, iodides, quinones or metal ions. Enzymes suitable for this purpose are, for example, peroxidases, which can significantly intensify the effect of smaller amounts of hydrogen peroxide. A use of certain metal ions or complexes may likewise be preferred. Suitable metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$, $Ce^{4+}$, $V^{3+}$, $Co^{2+}$, $Ru^{3+}$ and $Al^{3+}$. Here, $Zn^{2+}$, $Cu^{2+}$ and $Mn^{2+}$ are particularly suitable.

It has also proven to be advantageous if the oxidising agent compositions contain at least one stabiliser and/or complexing agent. Particularly preferred stabilisers are salicylic acid, alkali benzoates, in particular sodium benzoate, and phenacetin.

Complexing agents are substances that can complex metal ions. Preferred complexing agents are what are known as chelate complexing agents, that is to say substances that together with metal ions form cyclic compounds, wherein an individual ligand occupies more than one coordination point at a central atom, i.e. is at least "bidentate". Usual chelate complexing agents that are preferred within the scope of the present disclosure are, for example, polyoxycarboxylic acids, polyamines, ethylene diamine tetraacetic acid (EDTA), nitrilotriacetic acid (NTA), and hydroxyethane diphosphonic acids or alkali salts thereof. Complexing polymers, that is to say polymers that carry functional groups either in the main chain itself or in a side chain thereof, which groups can act as ligands and react with suitable metal atoms generally with formation of chelate complexes, can be used as contemplated herein. The polymer-bound ligands of the resultant metal complexes can originate here from just one macromolecule or can belong to different polymer chains. Complexing agents that are preferred as contemplated herein are nitrogen-containing polycarboxylic acids, in particular EDTA, and phosphonates, preferably hydroxyalkane or aminoalkane phosphonates and in particular aminoalkane phosphonates and in particular 1-hydroxyethane-1,1-diphosphonate (HEDP) or the di- or tetrasodium salt thereof and/or ethylenediamine tetramethylene phosphonate (EDTMP) or hexasodium salt thereof and/or diethylenetriamine pentamethylene phosphonate (DTPMP) or hepta- or octasodium salt thereof.

The at least one stabiliser and/or at least one complexing agent are generally contained in a total amount of from about 0.01 to about 3% by weight, preferably from about 0.03 to about 1.0% by weight, in relation to the total weight of the oxidising agent composition.

Besides the above-mentioned components present in the oxidising agent composition as contemplated herein and optionally provided components, the oxidising agent composition as contemplated herein usually contains water in an amount of generally from about 70 to about 95% by weight, preferably from about 78 to about 91% by weight, in relation to the weight of the oxidising agent composition.

Furthermore, the oxidising agent composition as contemplated herein can additionally contain auxiliaries and additives known to a person skilled in the art.

The oxidising agent composition as contemplated herein can be present in principle in the form of creams, emulsions, gels or surfactant-containing foaming solutions, such as shampoos, foam aerosols, foam formulations or other preparations which are suitable for use on keratin fibres, in particular human hair.

The oxidising agent composition as contemplated herein is preferably present in the form of a cream, an emulsion or a gel.

A further subject of the present disclosure is a packaging unit (kit of parts), comprising—packaged separately from one another— a) at least one container (C1), containing an agent (M1) for oxidative dyeing of keratin fibres (dye component), in particular human hair, and b) at least one container (C2), containing an oxidising agent composition (M2) containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water.

Preferred oxidising agent compositions (M2) are mentioned above. That said in respect of the oxidising agent compositions as contemplated herein and preferred as contemplated herein applies mutatis mutandis for the packaging units and kits as contemplated herein and preferred as contemplated herein.

A further subject of the present disclosure is a method for oxidative hair dyeing comprising the following method steps:

i) providing an agent for oxidative hair dyeing (M1) (dye component), ii) providing an oxidising agent composition (M2) containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water.

iii) mixing the agent (M1) with the oxidising agent composition (M2), preferably in a ratio by weight (M1):(M2) in the range of from about 1:0.8 to about 1:2.5, particularly preferably from about 1:1 to about 1:2, then directly thereafter iv) applying the mixture obtained in step iii) to the hair and leaving this mixture on the hair for a time of from about 1 to about 60 minutes, preferably from about 20 to about 45 minutes, at room temperature and/or at from about 30 to about 60° C., preferably at from about 32 to about 50° C.

v) rinsing the hair with water and/or a cleansing composition, and vi) optionally applying a post-treatment agent to the hair and optionally rinsing, then drying.

Preferred oxidising agent compositions (M2) are mentioned above. That said in respect of the oxidising agent compositions as contemplated herein and preferred as contemplated herein applies mutatis mutandis for the oxidative hair dyeing methods as contemplated herein and preferred as contemplated herein.

The ready-to-use agent formed of oxidising agent composition (M2) and oxidative dyeing agent (M1) (dye component) preferably have a pH value in the range of from about 6 to about 11. The ready-to-use agents preferably have an alkaline pH value. The ready-to-use agent particularly preferably has a pH value of from about 8.5 to about 11, preferably from about 9.5 to about 10.5. In order to adjust the pH value, suitable acidification and alkalising agents are mentioned above.

The term "room temperature" as contemplated herein denotes the temperature in the space in which a person usually uses a hair colouring agent, i.e. usually a bathroom or a hairdresser's salon, in which a temperature ranging from about 10 to about 29° C. prevails.

Oxidative Dyeing Agent (M1)

The oxidative dyeing agent contains at least one colour-changing component. Bleaching power boosters, which intensify the effect of the oxidising agent, and/or colouring components can be used as lightening agent as hair colour-changing component in the agent (M1).

In one embodiment the agent (M1) therefore contains a bleaching power booster. Within the scope of this present disclosure, peroxo compounds, and also compounds which produce aliphatic peroxocarboxylic acids and/or substituted perbenzoic acid under perhydrolysis conditions, carbonic acid derivatives, alkyl carbonates, alkyl carbamates, silyl carbonates and silyl carbamates can be used as bleaching power boosters. The bleaching power booster is preferably selected from ammonium peroxodisulfate, alkali metal peroxodisulfates, ammonium peroxomonosulfate, alkali metal hydrogen peroxomonosulfates, alkali metal peroxodiphosphates and alkaline earth metal peroxides. Particularly preferred bleaching power boosters are ammonium peroxodisulfate, potassium peroxodisulfate, sodium peroxodisulfate, potassium hydrogen peroxomonosulfate, potassium peroxodiphosphate, magnesium peroxide and barium peroxide. Particularly preferred are agents that, as bleaching power booster, contain at least one inorganic salt selected from peroxomonosulfates and/or peroxodisulfates. When performing the works for the present disclosure it proved to be particularly preferred if the agents (M1) contained at least two different peroxodisulfates. Here, preferred peroxodisulfate salts are combinations of ammonium peroxodisulfate and potassium peroxodisulfate and/or sodium peroxodisulfate. The at least one peroxo compound is generally contained in a total amount of from about 0.1 to about 95% by weight, preferably in an amount of from about 10 to about 70% by weight, exceptionally preferably from about 20 to about 45% by weight, in each case in relation to the total weight of the agent (M1).

The use of persulfate salts or peroxodisulfates is generally free from water and is implemented in the form of an optionally dedusted powder, paste or a shaped body pressed in a mould. The agent (M1) can contain a further bleaching power booster instead of or additionally to the solid peroxo compounds.

Although, in principle, there are no limitations in respect of the formulation of the agent (M1), it has proven to be preferable as contemplated herein if the agent (M1) is formulated free from water, if the agent (M1) contains an additional bleaching power booster as colour-changing component. In the sense of the present disclosure, "free from water" or "anhydrous" means a water content, in relation to the agent (M1), of less than about 5% by weight, in particular of less than about 2% by weight. Agents (M1) that contain less than about 0.1% by weight water can be particularly preferred. The agent (M1) is preferably formulated as powder or as an anhydrous paste.

In a further preferred embodiment the agent (M1) can contain at least one cationic pyridinium derivative as bleaching power booster. Preferred compounds are 4-acylpyridinium derivatives and 2-acylpyridinium derivatives. Particularly preferred here are 2-acetyl-1-methylpyridinium-p-toluene sulfonate and 4-acetyl-1-methylpyridinium-p-toluene sulfonate. Further preferred cationic pyridinium derivatives are cationic 3,4-dihydroisoquinolinium derivative. Particularly preferred is N-methyl-3,4-dihydroisoquinolinium-p-toluene sulfonate.

The bleaching power boosters used in addition to or instead of peroxo compounds are contained in the cosmetic agents as contemplated herein preferably in amounts of from about 0.05 to about 10% by weight, in particular in amounts of from about 0.2 to about 5% by weight, in each case in relation to the total weight of the agent (M1).

To further increase the lightening power, at least one optionally hydrated $SiO_2$ compound can additionally be added as bleaching booster to the agent (M1). Although even small amounts of the optionally hydrated $SiO_2$ compounds increase the lightening power, it can be preferred as contemplated herein to use the optionally hydrated $SiO_2$ compounds in amounts of from about 0.05% by weight to about 15% by weight, particularly preferably in amounts of from about 0.15% by weight to about 10% by weight, and very particularly preferably in amounts of from about 0.2% by weight to about 5% by weight, in each case in relation to the agent (M1). The specified amounts in each case reflect the content of the $SiO_2$ compounds (without the water component thereof) in the agents. Preferred optionally hydrated $SiO_2$ compounds are silica, the oligomers and polymers thereof, and the salts thereof. The optionally hydrated $SiO_2$ compounds can be present in different forms. The $SiO_2$ compounds are preferably used as contemplated herein in the form of silica gels or particularly preferably as water glass. Water glasses which are formed from a silicate of formula $(SiO_2)_n(Na_2O)_m(K_2O)_p$ are preferred as contemplated herein, wherein n stands for a positive rational number and m an p independently of one another stand for a positive rational number or for about 0, with the proviso that at least one of the parameters m or p is different from about 0 and the ratio between n and the sum of m and p is between from about 1:4 and about 4:1. In particular, metasilicates which are exemplified in accordance with the above formula by the ratio between n and the sum of m and p of <1 and which can be considered to be chain-like polymer structures of the anion $[SiO_3]^{2-}$ can be used with preference. Sodium metasilicate of formula $[NaSiO_3]_x$ is particularly preferred here.

In a further embodiment of the present disclosure the agent (M1) contains colouring components as hair colour-changing component. The agents as contemplated herein can therefore contain at least one hair-colouring component which can be present in the agent (M1) in addition to the lightening agent or without additional lightening agent. The hair-colouring component is preferably selected from the group including of at least one oxidation dye precursor product, from at least one substantive dye, and mixtures thereof.

Preferred agents for oxidatively dyeing keratin fibres (M1) are therefore exemplified in that they contain at least one oxidation dye precursor product. The agents contain, as oxidation dye precursor product, at least one oxidation dye precursor product of the developer type (developer component), preferably in combination with at least one oxidation dye precursor product of the coupler type (coupler component).

Preferred oxidation dye precursor products of the developer type are p-phenylenediamine derivatives. Preferred p-phenylendiamines are selected from one or more compounds of the group formed from p-phenylenediamine, p-toluenediamine, 2-chloro-p-phenylenediamine, 2,3-di methyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(2-hydroxyethyl)-p-phenylenediamine, 4-N,N-bis-(2-hydroxyethyl)amino-2-methylaniline, 4-N,N-bis-(2-hydroxyethyl)-amino-2-chloroaniline, 2-(2-hydroxyethyl)-p- phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxy methyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxane and physiologically acceptable salts thereof. Particularly preferred p-phenylenediamine derivatives as contemplated herein are selected from at least one compound of the group p-phenylenediamine, p-toluenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, 2-methoxymethyl-p-phenylenediamine and physiologically acceptable salts thereof.

It can also be further preferred to use, as developer component, compounds that contain at least two aromatic cores which are substituted with amino and/or hydroxyl groups. Preferred two-core developer components are selected in particular from at least one of the following compounds: N,N-bis-(2-hydroxyethyl)-N,N-bis(4'-aminophenyl)-1,3-diaminopropan-2-ol, N,N-bis-(2-hydroxyethyl)-N,N-bis-(4'-aminophenyl)-ethylenediamine, N,N'-bis-(4'-aminophenyl)tetramethylenediamine, N,N-bis-(2-hydroxyethyl)-N,N'-bis-(4'-aminophenyl)-tetramethylenediamine, N,N'-bis-(4-(methylamino)phenyl) tetramethylenediamine, N,N'-diethyl-N,N'-bis-(4'-amino-3'-methylphenyl)ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl) piperazine, N-(4'-aminophenyl)-p-phenylenediamine and 1,10-bis-(2',5'-diaminophenyl)-1,4,7,10-tetraoxadecane and physiologically acceptable salts thereof. Particularly preferred binuclear developer components are selected from N,N'-bis-(2-hydroxyethyl)-N,N'-bis-(4-aminophenyl)-1,3-diamino-propan-2-ol, bis-(2-hydroxy-5-aminophenyl)methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetraoxadecane or physiologically acceptable salts thereof.

It can also be preferred to use, as developer component, a p-aminophenol derivative or one of the physiologically compatible salts thereof. Preferred p-aminophenols are in particular p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(2-hydroxyethoxy)-phenol, 4-amino-2-methylphenol, 4-amino-2-hydroxymethylphenol, 4-amino-2-methoxymethyl-phenol, 4-amino-2-aminomethylphenol, 4-amino-2-(2-hydroxyethyl-aminomethyl)-phenol, 4-amino-2-(1,2-dihydroxyethyl)-phenol, 4-amino-2-fluorophenol, 4-amino-2-chlorophenol, 4-amino-2,6-dichlorophenol, 4-amino-2-(diethylaminomethyl)phenol and physiologically acceptable salts thereof. Particularly preferred compounds are p-aminophenol, 4-amino-3-methylphenol, 4-amino-2-aminomethylphenol, 4-amino-2-(1,2-dihydroxyethyl)phenol and 4-amino-2-(diethylaminomethyl)phenol.

The developer component can also be selected from o-aminophenol and derivatives thereof, such as 2-amino-4-methylphenol, 2-amino-5-methylphenol or 2-amino-4-chlorophenol.

The developer component may also be selected from heterocyclic developer components, for example from pyrimidine derivatives, pyrazole derivatives, pyrazolopyrimidine and pyrazolopyrazole derivatives or the physiologically acceptable salts thereof. Preferred pyrimidine derivatives are in particular the compounds 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine. Preferred pyrazole derivatives are in particular the compounds selected from 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-isopropylpyrazole, 4,5-diamino-3-methyl-1-isopropylpyrazole, 4-amino-5-(2-aminoethyl)amino-1,3-dimethylpyrazole and physiologically compatible salts thereof, but in particular 4,5-diamino-1-(2-hydroxyethyl) pyrazole. Preferred pyrazole pyrimidines are the compounds selected from pyrazolo[1,5-a]pyrimidin-3,7-diamine, 2,5-dimethyl-pyrazolo[1,5-a]pyrimidin-3J-diamine, pyrazolo[1,5-a]pyrimidin-3,5-diamine, 2,7-dimethyl-pyrazolo[1,5-a]pyrimidin-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)-amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidin-3,7-diamine, 2,6-dimethylpyrazolo[1,5-a]pyrimidin-3,7-diamine, 3-amino-7-dimethylamino-2,5-dimethylpyrazolo[1,5-a]pyrimidine and physiologically acceptable salts thereof and the tautomeric forms thereof, if a tautomeric equilibrium is provided. 2,3-diamino-6,7-dihydro-1H,5H-pyrazolo[1,2-a]pyrazol-1-one is preferred.

It may be preferred as contemplated herein to select, as developer component, at least one compound from the group formed from p-phenylenediamine, p-toluenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)3-diaminopropan-2-ol, bis-(2-hydroxy-5-aminophenyl)methane, 3-bis-(2,5-diaminophenoxy)propan-2-ol, N,N'-bis-(4-aminophenyl)-1,4-diazacycloheptane, 10-bis-(2,5-diaminophenyl)-1,4,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, and physiologically acceptable salts thereof. Very particularly preferred developer components are p-toluenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)-pyrazole and physiologically acceptable salts thereof.

The at least one developer component is preferably contained in a total amount of from about 0.0001 to about 8% by weight, preferably from about 0.01 to about 5% by weight, exceptionally preferably from about 0.1 to about 3% by weight, in each case in relation to the weight of the agent (M1).

Coupler components, within the scope of oxidative dyeing, do not alone form any significant colouration, but instead always require the presence of developer components. It is therefore preferred as contemplated herein for additionally at least one developer component to be used when at least one coupler component is used. Coupler components as contemplated herein allow at least one substitution of a chemical group of the coupler by the oxidised form of the developer component. Here, a covalent bond between coupler and developer component forms. Coupler components as contemplated herein are preferably selected as at least one compound from one of the following classes: m-aminophenol, o-aminophenol, m-diaminobenzene, o-diaminobenzene and/or derivatives thereof naphthalene derivatives with at least one hydroxy group; d- or trihydroxybenzene; pyridine derivatives; pyrimidine derivatives; certain indole derivatives and indoline derivatives; pyrazolone derivatives (for example 1-phenyl-3-methylpyrazol-5-one); morpholine derivatives (for example 6-hydroxybenzomorpholine or 6-aminobenzomorpholine); quinoxaline derivatives (for example 6-methyl-1,2,3,4-tetrahydroquinoxaline), and mixtures of two or more compounds from one or more of these classes.

Preferred m-aminophenol coupler components are selected from at least one compound from the group formed from 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamino)benzene, 3-ethylamino-4-methylphenol, 2,4-dichloro-3-aminophenol and physiologically acceptable salts thereof.

Preferred m-diaminobenzene coupler components are selected from at least one compound from the group formed from m-phenylenediamine, diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxy ethyl)-amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxy ethoxy)-5-methylphenylamine, 1-amino-3-bis-(2'-hydroxyethyl) aminobenzene and physiologically acceptable salts.

Preferred o-diaminobenzene coupler components are selected from at least one compound from the group formed from 3,4-diaminobenzoic acid and 2,3-diamino-1-methylbenzene and physiologically acceptable salts.

Preferred naphthalene derivatives having at least one hydroxy group are selected from at least one compound of the group formed from 1-naphthol, 2-methyl-1-naphthol, 2-hydroxy methyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene.

Preferred di- or trihydroxybenzenes and derivatives thereof are selected from at least one compound of the group formed form resorcinol, resorcinol monomethylether, 2-methylresorcinol, 5-methylresorcinol, 2,5-dimethylresorcinol, 2-chlororesorcinol, 4-chlororesorcinol, pyrogallol and 1,2,4-trihydroxybenzene.

Preferred pyridine derivatives are selected from at least one compound of the group formed from 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxy pyri dine, 3,5-diamino-2,6-dimethoxypyridine, 3,4-diaminopyridine, 2-(2-methoxy ethyl)amino-3-amino-6-methoxypyridine, 2-(4'-methoxyphenyl)amino-3-aminopyridine and physiologically acceptable salts thereof.

Preferred pyrimidine derivatives are selected from at least one compound of the group formed from 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and physiologically acceptable salts thereof.

Preferred indole derivatives are selected from at least one compound from the group formed from 4-hydroxyindole, 6-hydroxyindole and 7-hydroxyindole and physiologically acceptable salts thereof.

Preferred indoline derivatives are selected from at least one compound from the group formed from 4-hydroxyindoline, 6-hydroxyindoline and 7-hydroxyindoline and physiologically acceptable salts thereof.

Particularly preferred coupler components are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxy ethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxy pyri dine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or physiologically acceptable salts thereof. Very particularly preferred are resorcinol, 2-methylresorcinol, 5-amino-2-methylphenol, 3-aminophenol, diaminophenoxy)ethanol, 1,3-bis(2,4-diaminophenoxy) propane, 1-methoxy-2-amino-4-(2'-hydroxyethylamino) benzene, 2-amino-3-hydroxypyridine and 1-naphthol and one of the physiologically acceptable salts thereof.

The at least one coupler component is preferably contained in a total amount of from about 0.0001 to about 5% by weight, preferably from about 0.01 to about 3% by weight, in each case in relation to the weight of the agent (M1).

Here, developer components and coupler components are generally contained in approximately equimolar amounts relative to one another. If the equimolar use has also proven to be expedient, a certain excess of individual oxidation dye precursor products is not disadvantageous, and therefore developer components and coupler components can be used in a molar ratio of from about 1 to about 0.5 up to from about 1 to about 3, in particular from about 1 to about 1 up to from about 1 to about 2.

In a further embodiment the agents (M1) can contain at least one substantive dye as hair-colouring component. These are dyes which are drawn directly onto the hair and do not require an oxidative process to form the colour. Substantive dyes are divided into anionic, cationic and non-ionic substantive dyes. Nitrophenylenediamines, nitroaminophenols, azo dyes, anthraquinones or indophenols are conventional.

The at least one substantive dye is preferably contained in an amount of from about 0.0001 to about 5.0% by weight, preferably from about 0.001 to about 1.5% by weight, in each case in relation to the weight of the agent (M1). The total amount of substantive dyes is preferably at most about 1.0% by weight, in relation to the weight of the agent (M1).

Preferred anionic substantive dyes are the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromphenol blue and tetrabromphenol blue. Preferred cationic substantive dyes include cationic triphenylmethane dyes, for example Basic Blue 7, Basic Blue 26, Basic Violet 2 and Basic Violet 14, aromatic systems which are substituted with a quaternary nitrogen group, for example Basic Yellow 57, Basic Red 76, Basic Blue 99, Basic Brown 16 and Basic Brown 17, as well as substantive dyes containing a heterocycle having at least one quaternary nitrogen atom, in particular Basic Yellow 87, Basic Orange 31 and Basic Red 51. The cationic substantive dyes sold under the Arianor® trademark are likewise cationic substantive dyes particularly preferred as contemplated herein. Suitable non-ionic substantive dyes are in particular non-ionic nitro and quinone dyes and neutral azo dyes. Preferred non-ionic substantive dyes are the compounds known under the following international names or trade names: HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxy ethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol. Dye combinations that are preferred as contemplated herein are the combination of tetrabromophenol blue and Acid Red 92; tetrabromophenol blue and Acid Red 98; tetrabromophenol blue and Acid Red 94; tetrabromophenol blue and Acid Red 87 or tetrabromophenol blue and Acid Red 51.

In order to adjust a basic pH value of the agent (M1) and in particular to stabilise dye precursor products, the agent (M1) generally contains additionally at least one alkalising agent. The alkalising agents that can be used to adjust the pH value are typically selected from inorganic salts, in particular the alkali and alkaline earth metals, organic alkalising agents, in particular amines, basic amino acids and alkanolamines, and ammonia.

Organic alkalising agents are preferably selected from alkanolamines from primary, secondary or tertiary amines with a C2-C6 alkyl main body which carries at least one hydroxyl group. Alkanolamines that are very particularly preferred as contemplated herein are selected from the group 2-aminoethan-1-ol (monoethanolamine), 2-amino-2-methylpropan-1-ol and 2-amino-2-methyl-propane-1,3-diol. A preferred alkanolamine is monoethanolamine. Suitable basic amine acids are lysine, arginine and ornithine. The inorganic alkalising agents as contemplated herein are preferably selected from the group formed from sodium hydroxide, potassium hydroxide, calcium hydroxide, barium hydroxide, sodium phosphate, potassium phosphate, sodium silicate, potassium silicate, ammonium hydrogen carbonate, sodium hydrogen carbonate, potassium hydrogen carbonate, ammonium carbonate, sodium carbonate and potassium carbonate.

A further subject of the present disclosure is the use of an oxidising agent composition containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water, for oxidative dyeing of keratin fibres, in particular human hair.

Preferred oxidising agent compositions are mentioned above. That said in respect of the oxidising agent compositions as contemplated herein and preferred as contemplated herein applies mutatis mutandis for the use as contemplated herein and preferred as contemplated herein.

To summarise, the present disclosure relates to the following particularly preferred embodiments:

An oxidising agent composition containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water.

An oxidising agent composition containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water, wherein the oxidising agent composition has a viscosity of from about 500 to about 7000 mPas, preferably from about 1500 to about 4000 mPas, in each case measured at about 20° C., Haake MV 2.

An oxidising agent composition containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water, wherein the oxidising agent composition has a pH value of from about 1.0 to about 6.5, preferably from about 1.4 to about 5.5, particularly preferably from about 2.8 to about 4, exceptionally preferably from about 3 to about 3.8, in each case measured at about 20° C.

An oxidising agent composition containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water, wherein the water-in-oil emulsion contains mineral oil as oil(s).

An oxidising agent composition containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water, wherein the water-in-oil emulsion contains niosurfactant(s) as surfactant(s).

An oxidising agent composition containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water, wherein the sodium polyacrylate has a weight-average molar mass $M_w$ in the range of from about 1,000,000 to about 20,000,000 Dalton, preferably from about 6,000,000 to about 15,000,000 Dalton.

An oxidising agent composition containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water, wherein the sodium polyacrylate is contained in an amount of from about 0.1 to about 2% by weight, preferably from about 0.2 to about 1.5% by weight, in each case in relation to the weight of the oxidising agent composition.

An oxidising agent composition containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5-4.9% by weight water, wherein hydrogen peroxide is contained in an amount of from about 0.5 to about 23% by weight, preferably from about 2.5 to about 21% by weight, particularly preferably from about 4 to about 20% by weight, very particularly preferably from about 5 to about 18% by weight, exceptionally preferably from about 6 to about 12% by weight, in each case in relation to the weight of the oxidising agent composition.

An oxidising agent composition containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water, wherein the oxidising agent composition is present in the form of a cream, an emulsion or a gel.

A packaging unit (kit of parts) comprising—packaged separately from one another—
a) at least one container (C1), containing an agent (M1) for oxidative dyeing of keratin fibres (dye component), in particular human hair, and
b) at least one container (C2), containing an oxidising agent composition (M2) containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water.

A method for oxidative hair dyeing comprising the following method steps:
i) providing an agent for oxidative hair dyeing (M1),
ii) providing an oxidising agent composition (M2) containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water.
iii) mixing the agent (M1) with the oxidising agent composition (M2), preferably in a ratio by weight (M1):(M2) in the range of from about 1:0.8 to about 1:2.5, preferably from about 1:1 to about 1:2, then directly thereafter
iv) applying the mixture obtained in step iii) to the hair and leaving this mixture on the hair for a time of from about 1 to about 60 minutes, preferably from about 20 to about 45 minutes, at room temperature and/or at from about 30 to about 60° C., preferably at from about 32 to about 50° C.
v) rinsing the hair with water and/or a cleansing composition, and
vi) optionally applying a post-treatment agent to the hair and optionally rinsing, then drying.

Use of an oxidising agent composition containing hydrogen peroxide and at least one sodium polyacrylate pre-gelled in a water-in-oil emulsion, wherein the water-in-oil emulsion, in each case in relation to the weight of the water-in-oil emulsion, contains from about 40 to about 60% by weight sodium polyacrylate, a total of from about 25 to about 45% by weight oil(s), a total of from about 0.5 to about 4.9% by weight surfactant(s), and from about 0.5 to about 4.9% by weight water, for oxidative dyeing of keratin fibres, in particular human hair.

Use of an oxidising agent composition as contemplated herein for oxidative bleaching or lightening of keratin fibres, in particular human hair.

Use of an oxidising agent composition as contemplated herein as fixing agent in a method for permanent shaping of keratin fibres, in particular human hair.

EXAMPLES

TABLE 1

Oxidising agent composition as contemplated herein

| Ingredient | Sample weight (% by weight) |
| --- | --- |
| EDTA Na2 | 0.15 |
| Flocare ® DP/ES-502[1)] | 1.00 |
| Disodium pyrophosphate | 0.30 |
| Sodium benzoate | 0.04 |
| Hydrogen peroxide (50%) | 12.00 |
| Phosphoric acid (85%) | 0.04 |
| Water | to 100.00 |

[1)]Mixture of water, sodium polyacrylate, mineral oil, Trideceth-6 and C11-13 isoparaffin

TABLE 2

Oxidising agent composition comparison

| Ingredient | Sample weight (% by weight) |
| --- | --- |
| EDTA Na2 | 0.15 |
| Fatty alcohol sulfate Na C16-18 | 0.17 |
| Cetearyl alcohol | 1.62 |
| Eumulgin ® RO 40[1)] | 0.32 |
| Disodium pyrophosphate | 0.30 |
| Sodium benzoate | 0.04 |
| Hydrogen peroxide (50%) | 12.00 |
| Phosphoric acid (85%) | 0.04 |
| Water | to 100.00 |

[1)]PEG-40 Castor Oil

TABLE 3

Example 1 Time saving - Production (2 kg batch size)

| Production step | Time expenditure for oxidising agent composition as contemplated herein | Time expenditure for comparison oxidising agent composition |
| --- | --- | --- |
| Melting of the fat components (80° C.) | not applicable | 60 min. |
| Incorporation of Flocare ® DP/ES-502 | 10 min. | not applicable |
| Dissolution and addition of the dyes | 10 min. | 10 min. |
| Pre-emulsification of the batch | not applicable | 10 min. |
| Cooling of the batch to > approx. 30° C. | not applicable | 25 min. |
| Addition of hydrogen peroxide | 5 min. | 5 min. |
| SUM | 25 min. | 110 min. |

Example 2: Water Saving—Production (2 kg Batch Size)

Cooling was performed with water flowing through the cooling jacket. The longer are the cooling times for a batch, the higher is the consumption of cooling water. Example 1 shows a large water saving due to the omission of the cooling times.

Cooling time—production of the oxidising agent composition as contemplated herein: not applicable Cooling time—production of the comparison oxidising agent composition: approximately 25 min.

Example 2: Energy Saving—Production (2 kg Batch Size)

In order to have to produce an emulsion the fat constituents have to be belted by external heating for example. The longer are the heating times for a batch, the higher is the consumption of energy.

Example 1 shows a large energy saving due to the omission of the heating time.

Heating time—production of the oxidising agent composition as contemplated herein: not applicable Heating time—production of the comparison oxidising agent composition: approximately 60 min.

Colouring

TABLE 4

Dye preparation (first component (M1))

| | % by weight |
| --- | --- |
| Polyacrylic acid ammonium salt (active substance) | 0.075 |
| Decyl oleate | 2.1 |
| Sodium cetearyl sulfate | 1.3 |
| Cetearyl alcohol | 14.9 |
| Glyceryl stearate | 5.4 |
| Linoleamidopropyl PG-dimoniumchloride phosphate | 0.05 |
| EDTA | 0.8 |
| Monoethanolamine | 0.4 |
| Ammonia (25% by weight aqueous solution) | 8.0 |
| Ascorbic acid | 0.1 |
| Sodium dithionite | 0.1 |
| L-serine | 0.3 |
| Polyquaternium-2 | 0.1 |
| p-toluenediamine sulfate | 0.8 |
| Resorcinol | 0.2 |
| m-aminophenol | 0.04 |
| 4-chlororesorcinol | 0.2 |
| 2-amino-4-[(2-hydroxyethyl)amino]-anisol | 0.02 |
| Water | to 100 |

The above colouring preparation (M1) was mixed with the oxidising agent composition according to table 1 in the ratio by weight 1:1, applied to hair strands, and rinsed out after a reaction time of 45 minutes at room temperature using 25° C. warm water. The hair was then washed with a shampoo, post-treated with a rinse-off conditioner and blow-dried. Colouring with high intensity was attained.

Permanent Waving Agent

The present disclosure also relates to a method for straightening or permanently shaping keratin fibres, in which (i) the fibres are deformed with the aid of mechanical deformation aids, such as rollers or foam curlers, after, before or during step (ii), (ii) a waving or straightening agent, which contains at least one keratin-reducing substance, is applied to the fibres, (iii) the fibres are rinsed after a reaction time Z1, preferably after 5-60 minutes, particularly preferably after 10-30 minutes, and optionally dried, (iv) an oxidising agent composition as contemplated herein or preferred as contemplated herein is then applied to the fibres as fixing agent and is rinsed out again after a reaction time Z2, preferably after 1-30 minutes, particularly preferably after 5-20 minutes.

The waving agent presented in Table 5 below was produced as keratin-reducing preparation in the form of a PIT emulsion and as part of a two-part oxidative permanent waving system. The specified amounts relate to % by weight, unless stated otherwise.

TABLE 5

| Raw material | Sample amount (% by weight) |
|---|---|
| Emulgade ® CM | 10.00 |
| Water | 57.32 |
| Natrosol ® 250 HR | 0.25 |
| Ammonium Thioglycolate 71% | 17.83 |
| HEDP 60% | 0.30 |
| Ammonia 25% | 1.80 |
| Ammonium Bicarbonate F Food Grade | 8.80 |
| Plantapon ® ACG LC | 1.00 |
| Eumulgin ® L | 1.00 |
| Perfume | 0.50 |
| Merquat ® 100 | 0.05 |
| Gluadin ® W 40 BP | 0.05 |
| *Aloe Vera* Extract | 0.60 |
| Keratin Powder | 0.50 |
| Total | 100 |

Explanation of the Ingredients:
Emulgade® CM (BASF): Water: 63.5% by weight, Cetearyl Isononanoate: 15% by weight, Cetearyl Alcohol: 7.5% by weight, Ceteareth-20, 7.5% by weight, Glyceryl Stearate: 2.5% by weight Glycerol: 2.5% by weight, Ceteareth-12: 0.5% by weight, Cetyl Palmitate: 0.5% by weight, Benzoic Acid: 0.5% by weight
(Natrosol 250 HR, Ashland): Hydroxyethylcellulose
HEDP 60%: Etidronic acid (60% by weight in water)
Plantapon® ACG LC (BASF): Disodium Cocoyl Glutamate, 35% by weight
Eumulgin® L (BASF): PPG-1-PEG-9 Lauryl Glycol Ether
Merquat® 100 (Lubrizol): Polyquaternium-6, 40% by weight in water
Gluadin® W 40 BP (BASF): Hydrolyzed Wheat Protein, 42% by weight in water
The total water content of the produced waving agent was 71.02% by weight.

When using the waving agent for permanent waving treatments in combination with the oxidising agent composition according to Table 1 as fixing agent, very good shaping results were observed, wherein there was no, or only an extremely low development of odour as a result of thio compounds and ammonia.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An oxidising agent composition comprising hydrogen peroxide and at least one sodium polyacrylate pre-gelled in a water-in-oil emulsion, wherein the water-in-oil emulsion, in relation to the weight of the water-in-oil emulsion, comprises from about 40 to about 60% by weight sodium polyacrylate, from about 25 to about 45% by weight oil(s), from about 0.5 to about 4.9% by weight surfactant(s), and from about 0.5 to about 4.9% by weight water.

2. The oxidising agent composition according to claim 1, wherein the oxidising agent composition has a viscosity of from about 500 to about 7000 mPas, measured at 20° C., Haake MV 2.

3. The oxidising agent composition according to claim 1, wherein the oxidizing agent has a pH value of from about 1.0 to about 6.5, measured at 20° C.

4. The oxidising agent composition according to claim 1, wherein the water-in-oil emulsion comprises mineral oil as oil(s).

5. The oxidising agent composition according to claim 1, wherein the water-in-oil emulsion comprises niosurfactant(s) as surfactant(s).

6. The oxidising agent composition according to claim 1, wherein the sodium polyacrylate has a weight-average molar mass $M_w$ of from about 1,000,000 to about 20,000,000 Dalton.

7. The oxidising agent composition according to claim 1, wherein the sodium polyacrylate is present in an amount of from about 0.1 to about 2% by weight, in relation to the weight of the oxidising agent composition.

8. The oxidising agent composition according to claim 1, wherein hydrogen peroxide is present in an amount of from about 0.5 to about 23% by weight in relation to the weight of the oxidising agent composition.

9. The oxidising agent composition according to claim 1, wherein the oxidising agent composition is present in the form of a cream, an emulsion or a gel.

10. A packaging unit kit of parts comprising, packaged separately from one another:
    a) at least one container (C1), comprising an agent (M1) for oxidative dyeing of keratin fibres as a dye component, and
    b) at least one container (C2), comprising an oxidising agent composition (M2) according to claim 1.

11. A method for oxidative hair dyeing comprising the following method steps:
    i) providing an agent for oxidative hair dyeing (M1),
    ii) providing an oxidising agent composition (M2) according to claim 1,
    iii) mixing the agent (M1) with the oxidising agent composition (M2) to form a mixture,
    iv) applying the mixture to the hair and leaving the mixture on the hair for a time of from about 1 to about 60 minutes,
    v) rinsing the hair with water and/or a cleansing composition, and
    vi) optionally applying a post-treatment agent to the hair and optionally rinsing, then drying.

12. The oxidizing agent according to claim 1, wherein the oxidising agent composition has a viscosity of from about 1500 to about 4000 mPas, measured at 20° C., Haake MV 2.

13. The oxidising agent composition according to claim 1, wherein the oxidizing agent has a pH value of from about 1.4 to about 5.5, measured at 20° C.

14. The oxidising agent composition according to claim 1, wherein the oxidizing agent has a pH value of from about 2.8 to about 4, measured at 20° C.

15. The oxidising agent composition according to claim 1, wherein the oxidizing agent has a pH value of from about 3 to about 3.8, measured at 20° C.

16. The oxidising agent composition according to claim 1, wherein the sodium polyacrylate has a weight-average molar mass $M_w$ of from about 6,000,000 to about 15,000,000 Dalton.

\* \* \* \* \*